United States Patent [19]

Hashiba et al.

[11] Patent Number: 5,959,124
[45] Date of Patent: Sep. 28, 1999

[54] METHOD OF PREPARING MALEIC ANHYDRIDE BY VAPOR PHASE OXIDATION OF HYDROCARBON

[75] Inventors: Hideto Hashiba; Akiyoshi Nakajima; Shinichi Higashi, all of Hyogo, Japan

[73] Assignee: Nippon Shokubai Co., Ltd., Japan

[21] Appl. No.: 08/829,599

[22] Filed: Mar. 31, 1997

[30] Foreign Application Priority Data

| Apr. 1, 1996 | [JP] | Japan | 8-079019 |
| Apr. 2, 1996 | [JP] | Japan | 8-079851 |
| Oct. 9, 1996 | [JP] | Japan | 8-268235 |

[51] Int. Cl.$^6$ .................................................. C07D 307/60
[52] U.S. Cl. .......................................... 549/259; 549/260
[58] Field of Search ............................. 549/259; 502/209

[56] References Cited

U.S. PATENT DOCUMENTS

| 4,017,521 | 4/1977 | Schneider | 502/209 |
| 4,147,661 | 4/1979 | Higgins et al. | 502/209 |
| 4,151,116 | 4/1979 | Mc Dermott | 502/209 |
| 4,668,802 | 5/1987 | Contractor | 549/259 |
| 5,530,144 | 6/1996 | Tsurita et al. | 549/259 |

FOREIGN PATENT DOCUMENTS

| 0056183 | 12/1981 | European Pat. Off. . |
| 0362817 | 4/1989 | European Pat. Off. . |
| 0384749 | 2/1990 | European Pat. Off. . |
| 1567073 | 1/1977 | United Kingdom . |
| 96/252230 | 2/1996 | WIPO . |

OTHER PUBLICATIONS

WPI/Derwent, XP 002046612 (1989).
WPI/Derwent, XP 002046613 (1987).
European Search Report, EP 97 10 5316, Nov. 12, 1997.
Chem. Abstract–vol. 24: 59844 (1996).
Japanese Patap. No. 56–41816, Dec. 1979, Purifying Method for Wet Process Phosphoric Acid Solution.
Japanese Patap. No. 56–45815,Sep. 1979, Manufacture of Crystalline Vanadium–Phosphorus Oxide.
Japanese Patap. No. 59–132938, Jul. 1984, Vanadium–Phorphorus Oxide Catalyst, etc.
Japanese Patap. No. 57–111219, Dec. 1980, Substitutional Solid Solution, etc.
Japanese Patap. No., 5–15781,Jan. 1993, Vanadium–Phosphorus Oxide Type Oxidizing Catalyst etc.
Japanese Patap. No., 61–251678, Nov. 1986, Production of Maleic Anhydride.
Catalyst today, 1, (1987) 527–536, B. K. Hodnett.
Igarishi et al., "Effects of Consecutive Oxidation etc.", J. Phys. Chem., vol. 97, pp. 7065–7071, 1993.

Primary Examiner—Bernard Dentz
Attorney, Agent, or Firm—Omri M. Behr, Esq.

[57] ABSTRACT

A vanadium-phosphorus oxide having an X-ray diffraction spectrum (Cu—K$\alpha$) showing main peaks of the diffraction angle $2\theta(\pm0.2°)$ at 18.5°, 23.0°, 28.4°, 29.9°, and 43.1° and having the intensity ratio of the peaks of the diffraction angle $2\theta(\pm0.2°)$ at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle $2\theta(\pm0.2°)$ at 23.0° and 28.4°, a method for the production of the oxide, a catalyst for use in a vapor phase oxidation formed of the oxide, and a method for the partial vapor phase oxidation of a hydrocarbon.

6 Claims, 4 Drawing Sheets

METHOD OF PREPARING MALEIC ANHYDRIDE BY VAPOR PHASE OXIDATION OF HYDROCARBON

BACKGROUND OF THE INVENTION

1. Field of the Invention

This invention relates to a novel vanadium-phosphorus oxide possessing a specific X-ray diffraction pattern, a method for the production of the oxide, a catalyst for vapor phase oxidation formed of the oxide, and a method for partial vapor phase oxidation of a hydrocarbon.

2. Description of the Prior Art

Various studies have been being continued concerning vanadium-phosphorus oxides and researches on the physical properties of these oxides and on the development of uses therefor have been under way at the same time. Particularly, it is well known that vanadium-phosphorus oxides are effective in the production of maleic anhydride by the vapor phase oxidation of such hydrocarbons as butane, butene, and butadiene which have four carbon atoms (C4 hydrocarbons). It is also well known that the catalytically effective component of a vanadium-phosphorus oxide is divanadyl pyrophosphate, a crystalline oxide having the composition of $(VO)_2P_2O_7$. This divanadyl pyrophosphate is obtained by synthesizing vanadyl hydrogen orthophosphate $(VOHPO_4 \cdot 0.5\ H_2O)$, the precursory thereof, calcining the precursor, and further subjecting the calcined precursor to a so-called activating treatment by a calcination in the current of an inactive gas or the mixed gas of a hydrocarbon gas such as butane with air thereby effecting topotactic rearrangement of the precursor.

It is well known that maleic anhydride is obtained by subjecting n-butane, 1-butene, 2-butene, butadiene, or a mixture thereof (hereinafter referred to collectively as "C4 hydrocarbon") to a vapor phase oxidation in the presence of a vanadium-phosphorus oxide catalyst. Many improved vanadium-phosphorus oxide catalysts and methods for the production thereof have been already proposed.

Some of these improved vanadium-phosphorus oxide catalyst have been specified by methods of their preparations and others have been specified by patterns of their X-ray diffraction peaks (JP-A-53-61,588, JP-A-56-41,816, JP-A-56-45,815, JP-A-59-132,938, and JP-A-05-15,781). It is held that in the vanadium-phosphorus oxide catalysts, those having vanadium in a state approximating closely to tetravalence are more favorable for the production of maleic anhydride than those having vanadium in a state approximating closely to pentavalence (JP-A-50-35,088 and JP-A-56-41,816).

Improved reaction conditions for the vapor phase oxidation of a C4 hydrocarbon by the use of a vanadium-phosphorus oxide catalyst have been also proposed (JP-A-61-191,680 and JP-A-61-251,678).

Further, methods for the production of vanadium-phosphorus oxides as a catalyst for the production of maleic anhydride have been inserted in numerous pieces of literature besides the patent publications mentioned above. They are described in detail in B. K. Hodnett, ed., Catalysis Today, Vol. 1, No. 5 (1987), for example.

The conventional vanadium-phosphorus oxide, when used as a catalyst for a vapor phase oxidation such as, for example, in the production of maleic anhydride, manifests such a catalytic activity as is generally insufficient and is particularly inefficient at relatively low temperatures. In producing maleic anhydride under commercially favorable conditions, therefore, this catalyst is inevitably at a disadvantage in affording maleic anhydride only in an unduly low yield. Since the conventional vanadium-phosphorus oxide catalyst is prone to variation of the valency of vanadium, the production of a vanadium-phosphorus oxide catalyst vested with expected catalytic properties depends on chances. The production under discussion, to be successfully commercialized, therefore, entails an extremely detrimental problem of leaving the yield of maleic anhydride wholly at the mercy of the variation among lots of catalyst.

An object of this invention, therefore, is to find a solution to the drawbacks of the conventional vanadium-phosphorus oxide catalyst as mentioned above and provide a novel vanadium-phosphorus oxide for the vapor phase oxidation.

A further object of this invention is to provide a novel vanadium-phosphorus oxide possessing a specific X-ray diffraction pattern and a method for the production thereof.

Another object of this invention is to provide a novel vanadium-phosphorus oxide which can be manufactured with high repeatability as to the catalytic performance.

Still another object of this invention is to provide a catalyst formed of the vanadium-phosphorus oxide and used for a vapor phase oxidation.

Yet another object of this invention is to provide a method for the partial vapor phase oxidation of a hydrocarbon.

A further object of this invention is to provide a method for the production of maleic anhydride by the partial vapor phase oxidation of a hydrocarbon of four carbon atoms.

SUMMARY OF THE INVENTION

The objects described above are accomplished by a vanadium-phosphorus oxide having an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°.

The objects mentioned above are also accomplished by a method for the production of a vanadium-phosphorus oxide possessing the nature of having an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°, which method comprises causing a tetravalent vanadium compound to react with a phosphorus compound in an organic solvent at a temperature in the range of 60°–150° C. and firing the resultant product of the reaction.

The objects mentioned above are further accomplished by a method for the production of a vanadium-phosphorus oxide possessing the nature of having an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°, which method comprises reducing a pentavalent vanadium compound in an organic solvent, then causing the reduced compound to react with a phosphorus compound at a temperature in the range of 60°–150° C., and calcing the resultant reaction product.

The objects mentioned above are also accomplished by a catalyst for use in a vapor phase oxidation, containing a vanadium-phosphorus oxide having an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°.

The objects mentioned above are further accomplished by a method for the partial vapor phase oxidation of a hydrocarbon with a molecular oxygen-containing gas by the use of a vanadium-phosphorus oxide possessing the nature of having an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°.

The vanadium-phosphorus oxide of this invention shows an excellent activity as a catalyst for use in a vapor phase oxidation. In the production of maleic anhydride by the vapor phase oxidation of butane, for example, it manifests a high catalytic activity even at a low reaction temperature and permits production of maleic anhydride with a high selectivity and consequently in a high yield as compared with the conventional catalyst. In the commercial production of maleic anhydride, therefore, it allows a marked reduction in the cost of production.

Further, the vanadium-phosphorus oxide of this invention attains the production with high repeatability as to the catalytic performance. As a result, the vapor phase oxidation can be carried out with high reliability in a high yield, with the yield of the product aimed at not varied with the lots.

DESCRIPTION OF THE PREFERRED EMBODIMENT

Figure 1:
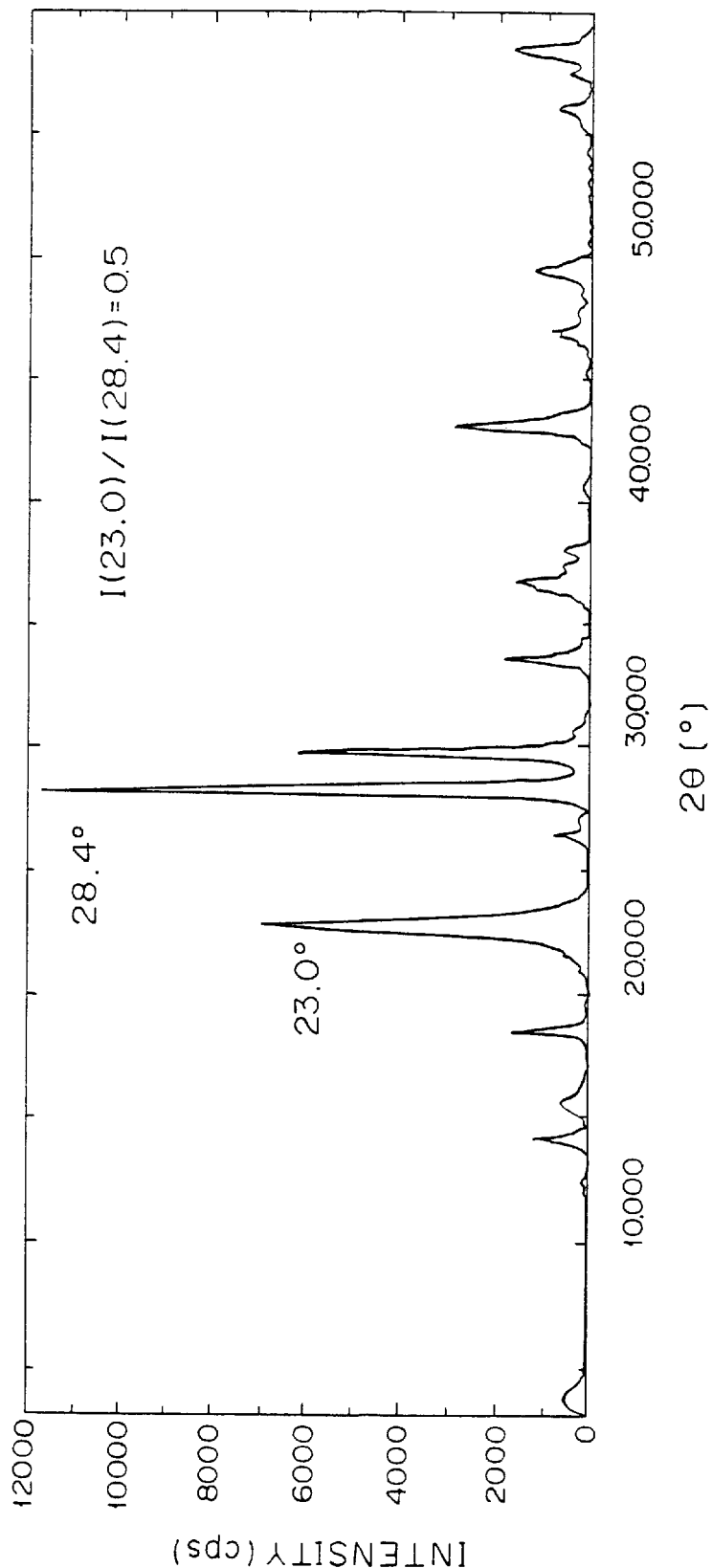
FIG. 1 is an X-ray diffraction spectrum (Cu—Kα) of the vanadium-phosphorus oxide obtained in Example 1. In the diagram, the horizontal axis constitutes the scale of the diffraction angle 2θ(±0.2°) and the vertical axis the peak intensity (cps).

The vanadium-phosphorus oxide according to the present invention has an X-ray diffraction spectrum (Cu—Kα) showing main peaks of the diffraction angle 2θ(±0.2°) at 18.5°, 23.0°, 28.4°, 29.9°, and 43.1° and having the intensity ratio of the peaks of the diffraction angle 2θ(±0.2°) at 23.0° and 28.4° in the following range $$0.3 \leq I\ (23.0)/I\ (28.4) \leq 0.7$$

wherein I (23.0) and I (28.4) respectively represent the intensities of the peaks of the diffraction angle 2θ(±0.2°) at 23.0° and 28.4°.

Appropriately, the vanadium-phosphorus oxide has the intensity ratio of the peaks, I (23.0)/I (28.4), in the range of 0.35–0.65, preferably in the range of 0.4–0.6.

The vanadium-phosphorus oxide according to the present invention is characterized in respect that it possesses a very strong peak at the diffraction angle 2θ(±0.2°) of 28.4° as compared with the conventional vanadium-phosphorus oxide.

The vanadium-phosphorus oxide according to the present invention is produced as follows.

Step (1)

The method of this invention starts from the reaction of a tetravalent vanadium compound with a phosphorus compound in an organic solvent at a temperature in the range of 60°–150° C. or from the reduction of a pentavalent vanadium compound followed by the reaction of the product of the reduction with a phosphorus compound at a temperature in the range of 60°–150° C. The latter method using the pentavalent vanadium compound is used particularly advantageously. First, therefore, the method using a pentavalent vanadium compound as a starting material will be described.

This method starts from the reduction of a pentavalent vanadium compound in an organic solvent. It is inferred that in consequence of this treatment of reduction, the pentavalent vanadium has the valency thereof changed to a level in the range of +3.9–4.1.

The term "organic solvent" as used in this invention means an organic solvent which combines the function of a reducing agent capable of reducing the pentavalent vanadium compound with the function of a reaction solvent. Any of the organic solvents which combine these functions can be used herein. As typical examples of the organic solvent, benzyl alcohols such as benzyl alcohol and benzyl alcohol derivatives resulting from the substitution of at least one member from among methyl benzyl alcohol, dimethyl benzyl alcohol, ethyl benzyl alcohol, and anisalcohol either with an alkyl group or alkoxy group of 1–3 carbon atoms may be cited. Among other organic solvents cited above, benzyl alcohol is used particularly advantageously.

The benzyl alcohol may be used in combination with an aliphatic alcohol such as methanol, ethanol, n-propanol, isopropanol, n-butanol, isobutanol, or amyl alcohol or with an aromatic aldehyde such as benzaldehyde, tolualdehyde, dimethyl benzaldehyde, or anisaldehyde on the condition that the reducing function of benzyl alcohol should not be impaired.

The term "pentavalent vanadium compound" as used in this invention embraces organic or inorganic compounds containing pentavalent vanadium. As typical examples of the compound, vanadium pentoxide and metavanadates such as ammonium metavanadate may be cited. Among other compounds cited above, vanadium pentoxide is advantageously used.

The term "phosphorus compound" as used in this invention embraces organic or inorganic compounds containing phosphorus. As typical examples of the compound, orthophosphoric acid, pyrophosphoric acid, phosphorous acid, polyphosphoric acid, and phosphorus pentoxide may be cited. Among other compounds cited above, about 99% (98–101%) orthophosphoric acid is used advantageously.

In a preferred embodiment of this invention, therefore, vanadium pentoxide is added to benzyl alcohol, then they are heated as stirred at a temperature in the range of 80°–150° C., preferably 100°–130° C., and the ensuing reduction of vanadium is continued until the solution turns to a blackish blue color and vanadium is thoroughly dissolved in benzyl alcohol. It is inferred that in consequence of this treatment of reduction, the pentavalent vanadium has the valency thereof changed to a level in the range of +3.9–4.1 as mentioned above. Subsequently, a solution of orthophosphoric acid in benzyl alcohol is added to the reduced vanadium solution mentioned above and they are stirred at a temperature in the range of 60°–150° C., preferably 80°–140° C., to induce a reaction.

If the temperature of the reduction treatment mentioned above is lower than 80° C., the reduction of the vanadium compound will not proceed or the treatment will consume much time. If this temperature conversely exceeds 150° C., the oxidation of the organic solvent will proceed and even entrain condensation possibly to the extent of rendering the separation of the organic solvent from the produced oxide difficult. In any event, by performing the reduction treatment at a temperature in the range of 80°–150° C., preferably 100°–130° C., the produced vanadium-phosphorus oxide is enabled to acquire the pattern of an X-ray diffraction spectrum and the intensity ratio of peaks mentioned above. The reduction treatment is performed until the solution turns to a blackish blue color and the vanadium is thoroughly dissolved. Generally, a period in the range of 2 to 10 hours suffices.

Properly, the vanadium compound and the phosphorus compound are used in such amounts that the vanadium/phosphorus atomic ratio may fall in the range of 1/0.9–1/1.2, preferably 1/0.95–1/1.1.

By performing the stirring action in the reaction mentioned above at a temperature in the range of 60–150° C., preferably 80°–140° C., the produced vanadium-phosphorus oxide is enabled to acquire the pattern of an X-ray diffraction spectrum and the intensity ratio of peaks mentioned above. For the reaction which is effected by the stirring, a period in the approximate range of 3–24 hours generally suffices.

Now, the method which uses a tetravalent vanadium compound as a starting material will be described.

In this method, a tetravalent vanadium compound is used as the starting material and it is dissolved in an organic solvent and caused to react with a phosphorus compound at a temperature in the range of 60°–150° C.

The term "tetravalent vanadium compound" as used in this invention means organic or inorganic compounds containing tetravalent vanadium. As typical examples of the compound, vanadium dioxide, vanadium oxydichloride, etc. may be cited. Among other vanadium compounds cited above, vanadium dioxide is used particularly advantageously.

The ratio of the amounts of the phosphorus compound and the organic solvent and that of the amounts of the vanadium compound and the phosphorus compound in this method are the same as those described with respect to the preceding method.

In a preferred embodiment of this invention, therefore, vanadium dioxide is added to benzyl alcohol, then they are heated as stirred at a temperature in the range of 80°–150° C., preferably 100°–130° C., until thorough dissolution of the vanadium compound, and a solution of orthophosphoric acid in benzyl alcohol is added to the vanadium compound solution, and they are stirred at a temperature in the range of 60°–150° C., preferably 80°–140° C., to induce a reaction.

In the dissolving treatment mentioned above, the possibility of the tetravalent vanadium compound being reduced to trivalent vanadium is nil. The lack of this possibility may be logically explained by a supposition that the benzyl alcohol is not fully capable of reducing tetravalent vanadium to trivalency.

By performing the stirring action in the reaction mentioned above at a temperature in the range of 60°–150° C., preferably 80°–140° C., the produced vanadium-phosphorus oxide is enabled to acquire the pattern of an X-ray diffraction spectrum and the intensity ratio of peaks mentioned above. For the reaction which is effected by the stirring, a period in the approximate range of 3–24 hours generally suffices.

In the method using a pentavalent vanadium compound as well as the method using a tetravalent vanadium compound as a starting material, it is appropriate to carry out the reaction by stirring the reaction system at a temperature in the range of 60°–150° C. and further continue the stirring until the reaction product is aged until thorough precipitation. If the reaction temperature is lower than 60° C., the reaction of the vanadium compound with the phosphorus compound will not proceed easily. Conversely, if the reaction temperature exceeds 150° C., the oxidation possibly to the extent of rendering the separation of the organic solvent from the produced oxide difficult.

Step (2)

At the step (2), the reaction product (precipitate) obtained at the step (1) is fired.

Specifically, the precipitate is washed, filtered, then dried in a stream of an inert gas or air at a temperature in the range of 100°–150° C., preferably 120° to 150° C., for a period in the approximate range of 6–24 hours, pulverized or molded in a prescribed shape, and thereafter calcined in an atmosphere of an oxygen-containing gas such as air or in an atmosphere of a mixed gas consisting of an inert gas with air at a temperature in the range of 350°–600° C., preferably 400°–550° C., for a period in the approximate range of 2–10 hours. Generally nitrogen is used as the inert gas mentioned above.

Step (3)

The method to be adopted for the activation at the step (3) has no particular limit to impose. Any of the methods of activation which are generally used for the preparation of oxide catalysts of this class can be adopted. The powder or mold fired at the step (2) is activated herein by being treated in a current of an inert gas at a temperature in the range of 600°–800° C., preferably 650°–750° C. or in a current of a mixed gas of a hydrocarbon gas such as butane with air at a temperature in the range of 350°–600° C., preferably 400°–450° C., for a period in the approximate range of 5–24 hours, preferably 10–24 hours.

Nitrogen is generally used as the inert gas in the activation mentioned above. As typical examples of the hydrocarbon to be used in the mixed gas, in addition to butane, hydrocarbons such as butene, butadiene, pentane, and isopentane which have 4 or 5 carbon atoms may be cited. When the activation is carried out in a current of a mixed gas of a hydrocarbon gas with air, it is proper to set the concentration of the hydrocarbon gas calculated as butane in the mixed gas generally at a level in the range of 0.5–10% by volume, preferably 1–5% by volume. When the activation is carried out in a current of an inert gas, since the temperature of treatment must be elevated, the surface area tends to decrease and the catalytic activity to decline. It is, therefore, advantageous to carry out the activation in the current of a mixed gas of a hydrocarbon gas with air.

When the vanadium-phosphorus oxide obtained by the method 1 mentioned above is used as a catalyst, it can be used as formed in a specific shape and the formation in the prescribed shape can be carried out in the presence of a molding aid. As typical examples of the molding aid, such inorganic substances as silica gel, alumina sol, and talc and such organic substances as graphite and fatty acid salts may be cited. The formation in the prescribed shape may be carried out in the presence of inorganic fibers.

The catalyst of this invention for the vapor phase oxidation can be used either in its unmodified form or after being formed in conjunction with such a carrier as silica, alumina, titania, silicon carbide, or ceramic substance and deposited on the carrier. The shape of this catalyst has no particular limit to impose. The catalyst may be used as pulverized. By the conventional forming methods such as tabletting and extrusion molding, the catalyst may be formed in the shape of spheres, cylinders, arches, or saddles.

The vanadium-phosphorus oxide manifests the behavior of a solid acid. By virtue of the nature of this solid acid, the vanadium-phosphorus oxide can be used as a catalyst for the partial catalytic vapor phase oxidation of a hydrocarbon, particularly an aliphatic hydrocarbon of 3 to 5 carbon atoms.

As typical examples of the catalytic vapor phase oxidation which is attainable herein, the production of maleic anhydride by the oxidation of butane, the production of methacrolein and methacrylic acid by the oxidation of isobutane, the production of methacrylic acid by the oxidation of methacrolein, the production of acrylonitrile by the ammoxidation of propane, and the production of methacrylic acid by the oxidehydrogenation of isobutyric acid maybe cited. It can be used particularly for selective oxidation of normal butane into maleic anhydride in the presence of molecular oxygen.

The catalyst of this invention for use in the vapor phase oxidation is formed of the vanadium-phosphorus oxide mentioned above. Besides the vanadium-phosphorus oxide, this catalyst is allowed to incorporate therein such alkali metals as potassium, sodium, rubidium, and cesium; such alkaline earth metals as magnesium, calcium, and barium; and such transition metals as iron, nickel, cobalt, ruthenium, rhodium, palladium, iridium, platinum, gold, silver, copper, manganese, tungsten, molybdenum, chromium, arsenic, antimony, bismuth, thallium, lead, and tin on the condition that the specific peaks of the X-ray diffraction and the intensity ratio of peaks, I (23.0)/I (28.4), should not be affected. When such a metal component is incorporated, the supply source thereof may be the oxide, nitrate, sulfate, carbonate, phosphate, or organic acid salt of the relevant metal.

The catalyst of this invention for use in the vapor phase oxidation is particularly advantageously used for the production of maleic anhydride by the vapor phase oxidation of butane as mentioned above.

Generally, n-butane is used for the butane in the oxidation. This n-butane may contain isobutane, butenes, propane, and pentanes in a small amount. While air constitutes itself an ideal oxygen source for the vapor phase oxidation, pure oxygen may be used instead. The oxygen source, when necessary, may be diluted with such an inert gas as steam or nitrogen. The n-butane concentration in the whole raw material gas is in the range of 0.5–10% by volume, preferably 0.5–4% by volume, and the oxygen concentration is in the range of 10–30% by volume. When the catalyst is used in a fixed bed, the spatial velocity of the feed gas is in the range of 500–10000 $hr^{-1}$, preferably 1000–5000 $hr^{-1}$. The reaction temperature is in the range of 300°–550° C., preferably 300°–450° C. The reaction maybe carried out under normal pressure or a reduced pressure. Generally, it is performed under normal pressure. Naturally, the catalyst may be used in the form of a fluidized bed in the place of the fixed bed.

Now, this invention will be described more specifically below with reference to working examples and controls. It should be noted, however, that this invention is not limited thereto. The conversion, selectivity, and yield mentioned in the working examples and the controls are defined as follows.

Conversion (mol %)=(Number of mols of butane reacted/number of mols of butane supplied)×100

Selectivity (mol %)=(Number of mols of maleic anhydride formed/number of mols of butane reacted)×100

Yield (mol %)=(number of mols of maleic anhydride formed/number of mols of butane supplied)×100

EXAMPLE 1

In 4000 ml of benzyl alcohol, 400 g of vanadium pentoxide ($V_2O_5$) was suspended and stirred and meanwhile heated at 120° C. and left reducing for 5 hours to effect thorough dissolution of vanadium pentoxide. A phosphoric acid solution was prepared by dissolving 435.4 g of 99% orthophosphoric acid in 1000 ml of benzyl alcohol and kept at 100° C. When the blackish blue solution of reduced vanadium and the phosphoric acid solution added thereto at 100° C. were kept heated at 120° C. for 10 hours, they produced a dark blue precipitate. The reaction solution slurry was left cooling and the formed precipitate was separated. The precipitate was washed with acetone and dried at 140° C. for 12 hours. Then, the resultant dry mass was formed into pellets, 5 mm in length and 5 mm in diameter. The pellets were calcined in a current of air at 500° C. for 4 hours, cooled to 400° C., swept with a current of a mixed gas consisting of n-butane and air and having a n-butane concentration of 1.5% by volume, heated to 500° C. at a temperature increasing rate of 1° C./minute, and activated at 500° C. for 12 hours.

The vanadium-phosphorus oxide obtained as described above had an X-ray diffraction spectrum as shown in FIG. 1. This X-ray diffraction spectrum showed main peaks of the diffraction angle2θ(±0.2°) at 18.5°, 23.0°, 28.4°, 29.9°, and 43.1° and had the intensity ratio of the peaks, I (23.0)/I (28.4), of 0.5.

A flow type reaction vessel, 25 mm in diameter and 300 mm in length, was packed with 100 g of the vanadium-phosphorus oxide mentioned above. A mixed gas containing n-butane and air and having a n-butane concentration of 1.5% by volume was introduced into the reaction vessel at a space velocity of 2000 $hr^{-1}$ and treated therein at a reaction temperature of 385° C. and 390° C. to effect vapor phase oxidation of n-butane. The results are shown in Table 1.

Control 1

In 4000 ml of isobutyl alcohol, 400 g of vanadium pentoxide was suspended and stirred and meanwhile heated at 105° C. and left reducing for 12 hours. The reduction of vanadium pentoxide did not proceed completely. A phosphoric acid solution was prepared by dissolving 435.4 g of 99% orthophosphoric acid in 1000 ml of isobutyl alcohol and kept at 100° C. When the vanadium solution and the phosphoric acid solution added thereto at 100° C. were kept heated at 105° C. and stirred for 10 hours, they produced a dark blue precipitate. The reaction solution slurry was left cooling and the formed precipitate was separated. The precipitate was washed with acetone and dried at 140° C. for 12 hours. Then, the resultant dry mass was formed into pellets, 5 mm in length and 5 mm in diameter. The pellets were calcined and activated in the same manner as in Example 1.

Figure 2:
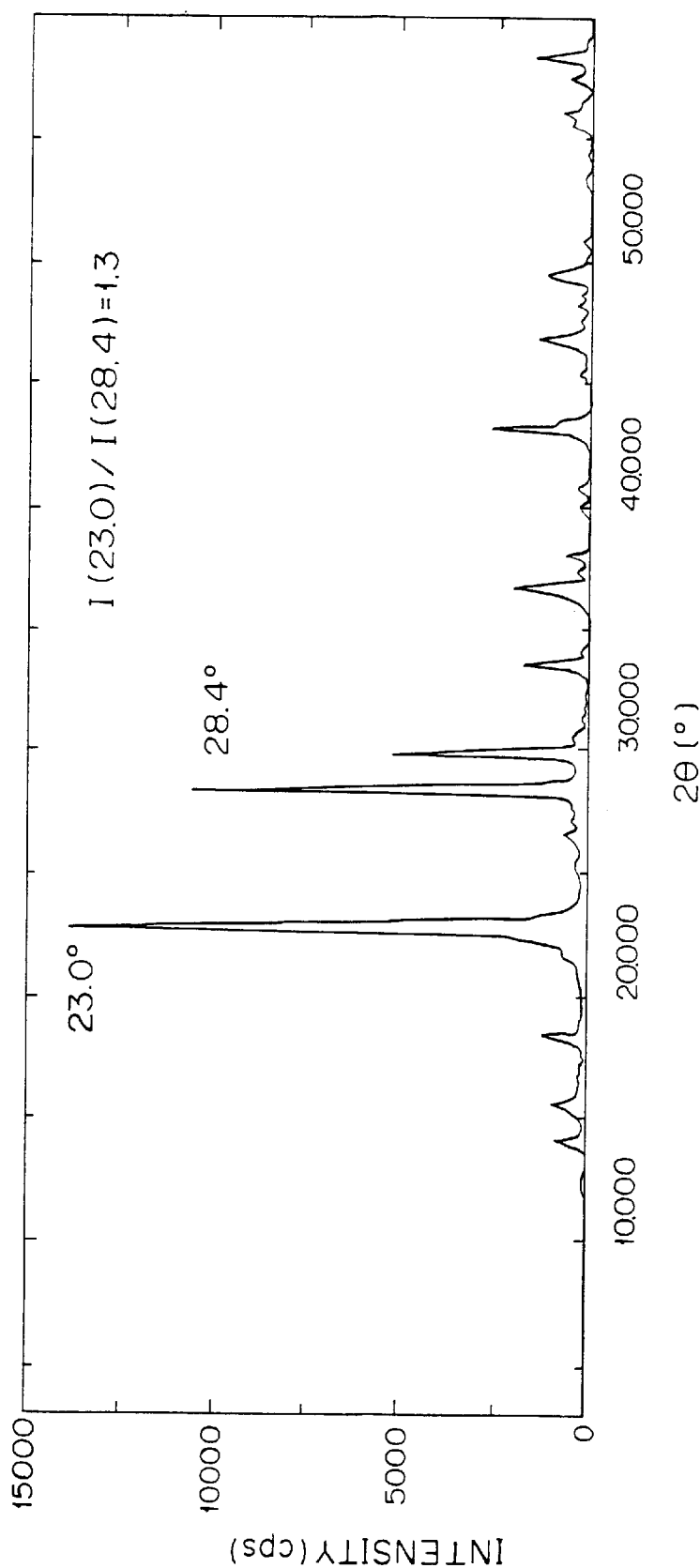
FIG. 2 is an X-ray diffraction spectrum (Cu—Kα) of the vanadium-phosphorus oxide obtained in Control 1. In the diagram, the horizontal axis and the vertical axis are identical with those of FIG. 1.

The vanadium-phosphorus oxide obtained as described above had an X-ray diffraction spectrum as shown in FIG. 2. This X-ray diffraction spectrum showed main peaks of the diffraction angle $2\theta(\pm 0.2°)$ at 18.5°, 23.0°, 28.4°, 29.9°, and 43.1° and had the intensity ratio of the peaks, I (23.0)/I (28.4), of 1.3.

A vapor phase oxidation of n-butane was carried out by following the procedure of Example 1 while using the vanadium-phosphorus oxide mentioned above and varying the reaction temperature as shown in Table 1. The results were as shown in Table 1.

EXAMPLE 2

In 4000 ml of benzyl alcohol, 400 g of vanadium pentoxide ($V_2O_5$) was suspended and stirred and meanwhile heated at 130° C. and left reducing for 3 hours to effect thorough dissolution of vanadium pentoxide. A phosphoric acid solution was prepared by dissolving 500.7 g of 99% orthophosphoric acid in 1000 ml of benzyl alcohol and kept at 80° C. When the blackish blue solution of reduced vanadium and the phosphoric acid solution added thereto at 80° C. were kept heated at 110° C. for 10 hours, they produced a dark blue precipitate. The reaction solution slurry was left cooling and the formed precipitate was separated. The precipitate was washed with acetone and dried at 140° C. for 12 hours. Then, the resultant dry mass was formed into pellets, 5 mm in length and 5 mm in diameter. The pellets were calcined and activated in the same manner as in Example 1.

Figure 3:
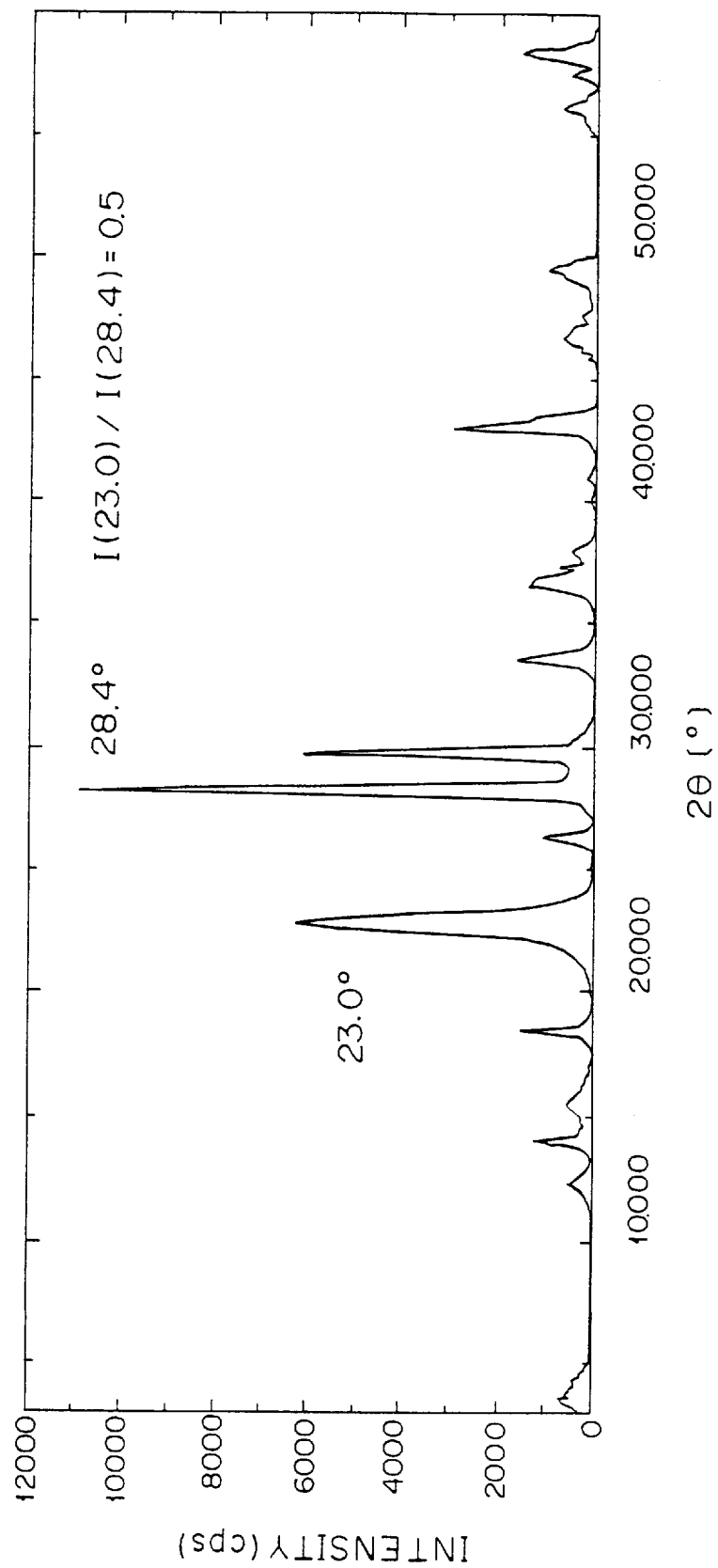
FIG. 3 is an X-ray diffraction spectrum (Cu—Kα) of the vanadium-phosphorus oxide obtained in Example 2. In the diagram, the horizontal axis and the vertical axis are identical with those of FIG. 1.

The vanadium-phosphorus oxide obtained as described above had an X-ray diffraction spectrum as shown in FIG. 3. This X-ray diffraction spectrum showed main peaks of the diffraction angle $2\theta(\pm 0.2°)$ at 18.5°, 23.0°, 28.4°, 29.9°, and 43.1° and had the intensity ratio of the peaks, I (23.0)/I (28.4), of 0.5.

A vapor phase oxidation of n-butane was carried out by following the procedure of Example 1 while using the vanadium-phosphorus oxide mentioned above and varying the reaction temperature as shown in Table 1. The results were as shown in Table 1.

EXAMPLE 3

In 4000 ml of benzyl alcohol, 400 g of vanadium dioxide ($VO_2$) was suspended and stirred and meanwhile heated at 130° C. and left reducing for 2 hours to effect thorough dissolution of vanadium dioxide. A phosphoric acid solution was prepared by dissolving 477.4 g of 99% orthophosphoric acid in 1000 ml of benzyl alcohol and kept at 80° C. When the blackish blue solution of reduced vanadium and the phosphoric acid solution added thereto at 80° C. were kept heated at 110° C. for 10 hours, they produced a dark blue precipitate. The reaction solution slurry was left cooling and the formed precipitate was separated. The precipitate was washed with acetone and dried at 140° C. for 12 hours. Then, the resultant dry mass was formed into pellets, 5 mm in length and 5 mm in diameter. The pellets were calcined and activated in the same manner as in Example 1.

Figure 4:
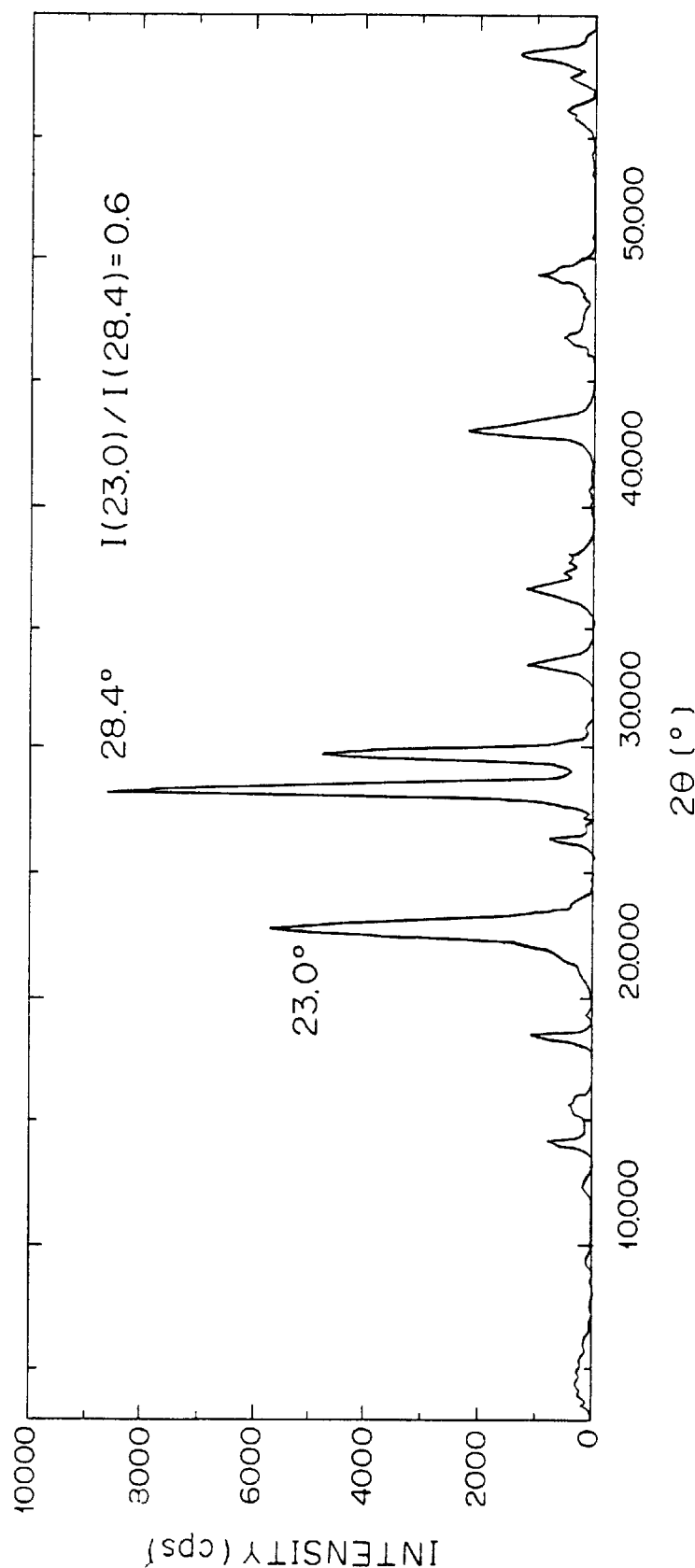
FIG. 4 is an X-ray diffraction spectrum (Cu—Kα) of the vanadium-phosphorus oxide obtained in Example 3. In the diagram, the horizontal axis and the vertical axis are identical with those of FIG. 1.

The vanadium-phosphorus oxide obtained as described above had an X-ray diffraction spectrum as shown in FIG. 4. This X-ray diffraction spectrum showed main peaks of the diffraction angle $2\theta(\pm 0.2°)$ at 18.5°, 23.0°, 28.4°, 29.9°, and 43.1° and had the intensity ratio of the peaks, I (23.0)/I (28.4), of 0.6.

A vapor phase oxidation of n-butane was carried out by following the procedure of Example 1 while using the vanadium-phosphorus oxide mentioned above and varying the reaction temperature as shown in Table 1. The results were as shown in Table 1.

TABLE

|  | Reaction temperature (°C.) | Conversion of n-butane (mol %) | Yield of maleic anhydride (mol %) | Selectivity of maleic anhydride (mol %) |
|---|---|---|---|---|
| Example 1 | 385 | 81.2 | 54.6 | 67.2 |
|  | 390 | 84.8 | 55.2 | 65.1 |
| Control 1 | 400 | 80.5 | 47.1 | 58.5 |
|  | 410 | 84.2 | 47.3 | 56.2 |
| Example 2 | 390 | 77.9 | 50.4 | 64.7 |
|  | 400 | 83.4 | 52.6 | 63.1 |
| Example 3 | 385 | 80.5 | 54.5 | 67.7 |
|  | 390 | 84.1 | 55.1 | 65.5 |

The entire disclosure of Japanese Patent Application No. 08-79,019 filed on Apr. 1, 1996, Japanese Patent Application No. 08-79,851 filed on Apr. 2, 1996, and Japanese Patent Application No. 08-268,235 filed on Oct. 9, 1996 including specification, claims, drawings and summary are incorporated herein by reference in its entirely.

What is claimed is:

1. A method for production of maleic anhydride which comprises subjecting butane to partial vapor phase oxidation with a molecular oxygen-containing gas in the presence of a catalyst which comprises a vanadium-phosphorus oxide having a x-ray diffraction spectrum (Cu—Kα) showing main peaks of the diffraction angle $2\theta(\pm 0.2°)$ at 18.5°, 23.0°, 28.4°, 29.9°, and 43.1° and having the intensity ratio of the peaks of the diffraction angle $2\theta(\pm 0.2°)$ at 23.0° and 28.4° in the following range $$0.4 \leq I\ (23.0)/I\ (28.4) \leq 0.6$$

wherein I (23.0) and I (28.4) respectively represent the intensities of the peaks of the diffraction angle $2\theta(\pm 0.2°)$ at 23.0° and 28.4°, and wherein said vanadium-phosphorus oxide is prepared by reacting a tetravalent vanadium compound with a phosphorus compound in benzyl alcohol or a benzyl alcohol having at least one alkyl or alkoxy group having 1 to 3 carbon atoms, at a temperature in the range of 60°–150° and firing the resultant product of the reaction.

2. A method according to claim 1, wherein an atomic ratio of vanadium/phosphorus is in the range of 1/0.9–1/1.2.

3. A method according to claim 1, wherein the reaction temperature is in the range of 80°–140° C.

4. A method for production of maleic anhydride which comprises subjecting butane to partial vapor phase oxidation with a molecular oxygen-containing gas in the presence of a catalyst which comprises a vanadium-phosphorus oxide having a x-ray diffraction spectrum (Cu—K$\alpha$) showing main peaks of the diffraction angle $2\theta(\pm 0.2°)$ at 18.5°, 23.0°, 28.4°, 29.9°, and 43.1° and having the intensity ratio of the peaks of the diffraction angle $2\theta(\pm 0.2°)$ at 23.0° and 28.4° in the following range $$0.4 \leq I\ (23.0)/I\ (28.4) \leq 0.6$$

wherein I (23.0°) and I (28.4°) respectively represent the intensities of the peaks of the diffraction angle $2\theta(\pm 0.2°)$ at 23.0° and 28.4°, and wherein said vanadium-phosphorous oxide is prepared by reducing a pentavalent vanadium compound in benzyl alcohol or a benzyl alcohol having at least one alkyl or alkoxy group having 1 to 3 carbon atoms, then reacting the reduced compound with a phosphorus compound at a temperature in the range of 60°–150° C., and firing the resultant reaction product.

5. A method according to claim 4, wherein the atomic ratio of vanadium/phosphorus is in the range of 1/0.9–1/1.2.

6. A method according to claim 4, wherein the reaction temperature is in the range of 80°–140° C.

* * * * *